(12) United States Patent
Carlino et al.

(10) Patent No.: US 11,969,341 B2
(45) Date of Patent: Apr. 30, 2024

(54) CARDIAC VALVE PROSTHESIS

(71) Applicant: Corcym S.r.l., Milan (IT)

(72) Inventors: Felice Giuseppe Carlino, Saluggia (IT); Marco Bussone, Saluggia (IT); Francesco Valle, Saluggia (IT); Monica Francesca Achiluzzi, Saluggia (IT)

(73) Assignee: Corcym S.r.l., Milan (IT)

( * ) Notice: Subject to any disclaimer, the term of this patent is extended or adjusted under 35 U.S.C. 154(b) by 0 days.

(21) Appl. No.: 18/056,908

(22) Filed: Nov. 18, 2022

(65) Prior Publication Data
US 2023/0078219 A1     Mar. 16, 2023

Related U.S. Application Data

(62) Division of application No. 17/056,382, filed as application No. PCT/IB2018/053640 on May 23, 2018, now Pat. No. 11,504,231.

(51) Int. Cl.
*A61F 2/24* (2006.01)

(52) U.S. Cl.
CPC .......... *A61F 2/2418* (2013.01); *A61F 2/2409* (2013.01); *A61F 2230/0054* (2013.01); *A61F 2230/006* (2013.01); *A61F 2250/0039* (2013.01)

(58) Field of Classification Search
CPC ........ A61F 2/24; A61F 2/2418; A61F 2/2412; A61F 2/2409; A61F 2/06
See application file for complete search history.

(56) References Cited

U.S. PATENT DOCUMENTS

| 3,143,742 A | 8/1964 | Cromie |
| 3,334,629 A | 8/1967 | Cohn |
| (Continued) | | |

FOREIGN PATENT DOCUMENTS

| CN | 101011298 A | 8/2007 |
| CN | 102869319 A | 1/2013 |
| (Continued) | | |

OTHER PUBLICATIONS

Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.

(Continued)

*Primary Examiner* — Seema Mathew
(74) *Attorney, Agent, or Firm* — Eversheds Sutherland (US) LLP; Christopher C. Bolten; Albert K. Heng

(57) ABSTRACT

A cardiac valve prosthesis including an armature for anchorage of the valve prosthesis at an implantation site. The armature defining a lumen for the passage of the blood flow and having a longitudinal axis, and a set of prosthetic valve leaflets supported by said armature and configured to move, under the action of blood flow, in a radially divaricated condition to enable the flow of blood through said lumen in a first direction, and in a radially contracted condition, in which said valve leaflets co-operate with one another and block the flow of blood through the prosthesis in the direction opposite said first direction. The armature including an annular part and a pattern of arches struts carried by said annular part, said pattern of arched struts having proximal ends connected to said annular part, and distal ends spaced axially from the proximal ends and opposite said annular part, a plurality of sets of anchoring formations configured to protrude radially outwardly of said annular (Continued)

part, each set being supported by a least one of said annular part and a corresponding arched strut, and a plurality of support posts, each support post being supported by adjacent arched struts, wherein the sets of anchoring formations alternate with the support posts around said longitudinal axis.

19 Claims, 8 Drawing Sheets

(56) References Cited

U.S. PATENT DOCUMENTS

| | | |
|---|---|---|
| 3,363,442 A | 1/1968 | Kennedy et al. |
| 3,409,013 A | 11/1968 | Henry et al. |
| 3,514,131 A | 5/1970 | McKinney et al. |
| 3,540,431 A | 11/1970 | Mobin-Uddin et al. |
| 3,546,710 A | 12/1970 | Shumakov et al. |
| 3,574,865 A | 4/1971 | Hamaker |
| 3,587,115 A | 6/1971 | Shiley et al. |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,011,947 A | 3/1977 | Sawyer |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,220,151 A | 9/1980 | Whitney |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,601,706 A | 7/1986 | Aillon |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,684,364 A | 8/1987 | Sawyer et al. |
| 4,692,164 A | 9/1987 | Dzemeshkevich et al. |
| 4,710,192 A | 12/1987 | Liotta et al. |
| 4,722,725 A | 2/1988 | Sawyer et al. |
| 4,732,152 A | 3/1988 | Wallsten et al. |
| 4,733,665 A | 3/1988 | Palmaz |
| 4,758,151 A | 7/1988 | Arru et al. |
| 4,777,951 A | 10/1988 | Cribier et al. |
| 4,784,644 A | 11/1988 | Sawyer et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,057,092 A | 10/1991 | Webster, Jr. |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,181,911 A | 1/1993 | Shturman |
| 5,201,757 A | 4/1993 | Heyn et al. |
| 5,217,483 A | 6/1993 | Tower |
| 5,232,445 A | 8/1993 | Bonzel |
| 5,272,909 A | 12/1993 | Nguyen et al. |
| 5,287,848 A | 2/1994 | Cubb et al. |
| 5,295,958 A | 3/1994 | Shturman |
| 5,300,086 A | 4/1994 | Gory et al. |
| 5,304,189 A | 4/1994 | Goldberg et al. |
| 5,312,393 A | 5/1994 | Mastel |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,433,723 A | 7/1995 | Lindenberg et al. |
| 5,443,446 A | 8/1995 | Shturman |
| 5,445,608 A | 8/1995 | Chen et al. |
| 5,445,646 A | 8/1995 | Euteneuer et al. |
| 5,449,384 A | 9/1995 | Johnson |
| 5,480,424 A | 1/1996 | Cox |
| 5,489,294 A | 2/1996 | McVENES et al. |
| 5,489,296 A | 2/1996 | Love et al. |
| 5,489,297 A | 2/1996 | Duran |
| 5,496,346 A | 3/1996 | Horzewski et al. |
| 5,500,014 A | 3/1996 | Quijano et al. |
| 5,505,689 A | 4/1996 | Kramer et al. |
| 5,507,767 A | 4/1996 | Maeda et al. |
| 5,522,884 A | 6/1996 | Wright |
| 5,545,209 A | 8/1996 | Roberts et al. |

(56) References Cited

U.S. PATENT DOCUMENTS

| | | |
|---|---|---|
| 5,545,211 A | 8/1996 | An et al. |
| 5,545,214 A | 8/1996 | Stevens |
| 5,545,215 A | 8/1996 | Duran |
| 5,554,185 A | 9/1996 | Block et al. |
| 5,556,414 A | 9/1996 | Turi |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,662,712 A | 9/1997 | Pathak et al. |
| 5,665,115 A | 9/1997 | Cragg |
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,693,083 A | 12/1997 | Baker et al. |
| 5,695,498 A | 12/1997 | Tower |
| 5,698,307 A | 12/1997 | Levy |
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,772,693 A | 6/1998 | Brownlee |
| 5,776,187 A | 7/1998 | Krueger et al. |
| 5,782,809 A | 7/1998 | Umeno et al. |
| 5,782,811 A | 7/1998 | Samson et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,849,005 A | 12/1998 | Garrison et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,860,996 A | 1/1999 | Urban et al. |
| 5,861,028 A | 1/1999 | Angell |
| 5,868,783 A | 2/1999 | Tower |
| 5,871,489 A | 2/1999 | Ovil |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,951,600 A | 9/1999 | Lemelson |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,530 A | 1/2000 | Goicoechea |
| 6,010,531 A | 1/2000 | Donlon et al. |
| 6,019,739 A | 2/2000 | Rhee et al. |
| 6,019,756 A | 2/2000 | Mueller et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,030,360 A | 2/2000 | Biggs |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,014 A | 4/2000 | Jang |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,090,099 A | 7/2000 | Samson et al. |
| 6,106,497 A | 8/2000 | Wang |
| 6,110,200 A | 8/2000 | Hinnenkamp |
| 6,110,201 A | 8/2000 | Quijano et al. |
| 6,125,852 A | 10/2000 | Stevens et al. |
| 6,139,572 A | 10/2000 | Campbell et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,174,307 B1 | 1/2001 | Daniel et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,251,093 B1 | 6/2001 | Valley et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,312,465 B1 | 11/2001 | Griffin et al. |
| 6,338,735 B1 | 1/2002 | Stevens |
| 6,346,071 B1 | 2/2002 | Mussivand |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran et al. |
| 6,368,355 B1 | 4/2002 | Uflacker |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |

(56) References Cited

U.S. PATENT DOCUMENTS

| | | |
|---|---|---|
| 6,395,017 B1 | 5/2002 | Dwyer et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,416,474 B1 | 7/2002 | Penner et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,366 B1 | 10/2002 | Seguin |
| 6,461,382 B1 | 10/2002 | Cao |
| 6,468,303 B1 | 10/2002 | Amplatz et al. |
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,520,987 B1 | 2/2003 | Plante |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,607,553 B1 | 8/2003 | Healy et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,629,534 B1 | 10/2003 | St. Goar et al. |
| 6,635,068 B1 | 10/2003 | Dubrul et al. |
| 6,641,558 B1 | 11/2003 | Aboul-Hosn et al. |
| 6,645,197 B2 | 11/2003 | Garrison et al. |
| 6,645,220 B1 | 11/2003 | Huter et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,679,911 B2 | 1/2004 | Burgermeister |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 | 4/2004 | Wilder et al. |
| 6,719,789 B2 | 4/2004 | Cox |
| 6,726,648 B2 | 4/2004 | Kaplon et al. |
| 6,726,651 B1 | 4/2004 | Robinson et al. |
| 6,726,712 B1 | 4/2004 | Raeder-Devens et al. |
| 6,726,713 B2 | 4/2004 | Schaldach et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,161 B2 | 8/2004 | Brown et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,913,618 B2 | 7/2005 | Denardo et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,945,957 B2 | 9/2005 | Freyman |
| 6,951,571 B1 | 10/2005 | Srivastava |
| 6,964,673 B2 | 11/2005 | Tsugita et al. |
| 6,966,924 B2 | 11/2005 | Holmberg |
| 6,968,607 B2 | 11/2005 | Motsenbocker |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,981,942 B2 | 1/2006 | Khaw et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,646 B2 | 1/2006 | Clerc et al. |
| 6,991,649 B2 | 1/2006 | Sievers |
| 7,001,423 B2 | 2/2006 | Euteneuer et al. |
| 7,007,396 B2 | 3/2006 | Rudko et al. |
| 7,011,681 B2 | 3/2006 | Vesely |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,018,408 B2 | 3/2006 | Bailey et al. |
| 7,021,114 B2 | 4/2006 | Perreault |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,077,801 B2 | 7/2006 | Haverich |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,144,364 B2 | 12/2006 | Barbut et al. |
| 7,147,663 B1 | 12/2006 | Berg et al. |
| 7,153,324 B2 | 12/2006 | Case et al. |
| 7,156,872 B2 | 1/2007 | Strecker |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |

(56) References Cited

U.S. PATENT DOCUMENTS

| | | |
|---|---|---|
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheime et al. |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,467 B2 | 3/2008 | Lutter |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| RE40,377 E | 6/2008 | Williamson, IV et al. |
| 7,381,218 B2 | 6/2008 | Schreck |
| 7,381,220 B2 | 6/2008 | Macoviak et al. |
| 7,384,411 B1 | 6/2008 | Condado |
| 7,393,360 B2 | 7/2008 | Spenser et al. |
| 7,399,315 B2 | 7/2008 | Iobbi |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,455,690 B2 | 11/2008 | Cartledge et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,843 B1 | 9/2009 | Escano et al. |
| 7,591,848 B2 | 9/2009 | Allen |
| 7,618,432 B2 | 11/2009 | Pedersen et al. |
| 7,618,446 B2 | 11/2009 | Andersen et al. |
| 7,618,447 B2 | 11/2009 | Case et al. |
| 7,635,386 B1 | 12/2009 | Gammie |
| 7,648,528 B2 | 1/2010 | Styrc |
| 7,682,390 B2 | 3/2010 | Seguin |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,780,726 B2 | 8/2010 | Seguin |
| 7,785,341 B2 | 8/2010 | Forster et al. |
| 7,806,919 B2 | 10/2010 | Bloom et al. |
| 7,806,927 B2 | 10/2010 | Styrc |
| 7,857,845 B2 | 12/2010 | Stacchino et al. |
| 7,892,281 B2 | 2/2011 | Seguin et al. |
| 7,896,915 B2 | 3/2011 | Guyenot et al. |
| 7,959,672 B2 | 6/2011 | Salahieh et al. |
| 7,972,378 B2 | 7/2011 | Tabor et al. |
| 7,981,153 B2 | 7/2011 | Fogarty et al. |
| 7,993,392 B2 | 8/2011 | Righini et al. |
| 8,006,535 B2 | 8/2011 | Righini et al. |
| 8,016,882 B2 | 9/2011 | Macoviak et al. |
| 8,025,695 B2 | 9/2011 | Fogarty et al. |
| 8,034,103 B2 | 10/2011 | Burriesci et al. |
| 8,043,360 B2 | 10/2011 | McNamara et al. |
| 8,048,153 B2 | 11/2011 | Salahieh et al. |
| 8,057,539 B2 | 11/2011 | Ghione et al. |
| 8,070,799 B2 | 12/2011 | Righini et al. |
| 8,070,802 B2 | 12/2011 | Lamphere et al. |
| 8,080,053 B2 | 12/2011 | Satasiya et al. |
| 8,083,793 B2 | 12/2011 | Lane et al. |
| 8,105,375 B2 | 1/2012 | Navia et al. |
| 8,109,996 B2 | 2/2012 | Stacchino et al. |
| 8,114,154 B2 | 2/2012 | Righini et al. |
| 8,167,935 B2 | 5/2012 | McGuckin, Jr. et al. |
| 8,211,169 B2 | 7/2012 | Lane et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,298,244 B2 | 10/2012 | Garcia et al. |
| 8,323,335 B2 | 12/2012 | Rowe et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,454,686 B2 | 6/2013 | Alkhatib |
| 8,470,024 B2 | 6/2013 | Ghione et al. |
| 8,475,521 B2 | 7/2013 | Suri et al. |
| 8,486,137 B2 | 7/2013 | Suri et al. |
| 8,535,373 B2 | 9/2013 | Stacchino et al. |
| 8,539,662 B2 | 9/2013 | Stacchino et al. |
| 8,540,767 B2 | 9/2013 | Zhang |
| 8,540,768 B2 | 9/2013 | Stacchino et al. |
| 8,579,964 B2 | 11/2013 | Lane et al. |
| 8,579,966 B2 | 11/2013 | Seguin et al. |
| 8,597,348 B2 | 12/2013 | Rowe et al. |
| 8,753,393 B2 | 6/2014 | Strasly et al. |
| 8,808,369 B2 | 8/2014 | Suri |
| 8,822,219 B2 | 9/2014 | Strasly et al. |
| 8,834,563 B2 | 9/2014 | Righini |
| 8,840,661 B2 | 9/2014 | Manasse |
| 8,920,492 B2 | 12/2014 | Stacchino et al. |
| 9,161,836 B2 | 10/2015 | Rolando et al. |
| 9,186,249 B2 | 11/2015 | Rolando et al. |
| 9,248,017 B2 | 2/2016 | Rolando et al. |
| 9,289,289 B2 | 3/2016 | Rolando et al. |
| 9,415,567 B2 * | 8/2016 | Sogard ................. B32B 27/304 |
| 9,486,313 B2 | 11/2016 | Stacchino et al. |
| 9,848,981 B2 * | 12/2017 | Suri ...................... A61F 2/2418 |
| 9,867,695 B2 | 1/2018 | Stacchino et al. |
| 9,895,223 B2 | 2/2018 | Stacchino et al. |
| 10,098,733 B2 | 10/2018 | Righini |
| 10,201,418 B2 * | 2/2019 | Biadillah ............. A61F 2/2418 |
| 10,709,555 B2 | 7/2020 | Schreck et al. |
| 10,799,555 B2 * | 10/2020 | Gutierrez ............. A61K 39/015 |
| 10,973,629 B2 * | 4/2021 | Levi ..................... A61F 2/2418 |
| 11,185,405 B2 * | 11/2021 | Girard .................. A61F 2/2469 |
| 11,197,754 B2 * | 12/2021 | Saffari ................. A61F 2/2418 |
| 11,357,624 B2 * | 6/2022 | Guyenot ............. A61F 2/2442 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044591 A1 | 11/2001 | Stevens et al. |
| 2001/0044647 A1 | 11/2001 | Pinchuk et al. |
| 2001/0049558 A1 | 12/2001 | Liddicoat et al. |
| 2002/0010508 A1 | 1/2002 | Chobotov |
| 2002/0029014 A1 | 3/2002 | Jayaraman |
| 2002/0029075 A1 | 3/2002 | Leonhardt |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |

(56) References Cited

U.S. PATENT DOCUMENTS

| | | |
|---|---|---|
| 2002/0045929 A1 | 4/2002 | Diaz |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099431 A1 | 7/2002 | Armstrong et al. |
| 2002/0103533 A1 | 8/2002 | Langberg et al. |
| 2002/0107531 A1 | 8/2002 | Schreck et al. |
| 2002/0107565 A1 | 8/2002 | Greenhalgh |
| 2002/0111674 A1 | 8/2002 | Chouinard et al. |
| 2002/0117264 A1 | 8/2002 | Rinaldi et al. |
| 2002/0123802 A1 | 9/2002 | Snyders |
| 2002/0128702 A1 | 9/2002 | Menz et al. |
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0033000 A1 | 2/2003 | DiCaprio et al. |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1* | 8/2003 | Figulla ............... A61F 2/2418 623/2.38 |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191521 A1 | 10/2003 | Denardo et al. |
| 2003/0191528 A1 | 10/2003 | Quijano et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMATTEO et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127848 A1 | 7/2004 | Freyman |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0147993 A1 | 7/2004 | Westlund et al. |
| 2004/0153146 A1 | 8/2004 | Lashinski et al. |
| 2004/0167573 A1 | 8/2004 | Williamson, IV et al. |
| 2004/0167620 A1 | 8/2004 | Ortiz et al. |
| 2004/0186558 A1 | 9/2004 | Pavcnik et al. |
| 2004/0186563 A1* | 9/2004 | Lobbi ............... A61F 2/2418 623/2.11 |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0236170 A1 | 11/2004 | Kim |
| 2004/0249413 A1 | 12/2004 | Allen et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |

(56) References Cited

U.S. PATENT DOCUMENTS

| | | |
|---|---|---|
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096993 A1 | 5/2005 | Pradhan et al. |
| 2005/0104957 A1 | 5/2005 | Okamoto et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0165480 A1 | 7/2005 | Jordan et al. |
| 2005/0166389 A1 | 8/2005 | Perreault et al. |
| 2005/0182486 A1 | 8/2005 | Gabbay |
| 2005/0187616 A1 | 8/2005 | Realyvasquez |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0251251 A1 | 11/2005 | Cribier |
| 2005/0261759 A1 | 11/2005 | Lambrecht et al. |
| 2005/0267493 A1 | 12/2005 | Schreck et al. |
| 2005/0267529 A1 | 12/2005 | Crockett et al. |
| 2005/0278010 A1 | 12/2005 | Richardson |
| 2005/0283232 A1 | 12/2005 | Gabbay |
| 2005/0283962 A1 | 12/2005 | Boudjemline |
| 2006/0004436 A1 | 1/2006 | Amarant et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0025855 A1 | 2/2006 | Lashinski et al. |
| 2006/0029659 A1 | 2/2006 | Panzardi |
| 2006/0030922 A1 | 2/2006 | Dolan |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0063199 A1 | 3/2006 | Elgebaly et al. |
| 2006/0064054 A1 | 3/2006 | Sakakine et al. |
| 2006/0073592 A1 | 4/2006 | Sun et al. |
| 2006/0074271 A1 | 4/2006 | Cotter |
| 2006/0074484 A1 | 4/2006 | Huber |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0095025 A1 | 5/2006 | Levine et al. |
| 2006/0095117 A1 | 5/2006 | Popelar et al. |
| 2006/0100639 A1 | 5/2006 | Levin et al. |
| 2006/0100685 A1 | 5/2006 | Seguin et al. |
| 2006/0116757 A1 | 6/2006 | Lashinski et al. |
| 2006/0135962 A1 | 6/2006 | Kick et al. |
| 2006/0135964 A1 | 6/2006 | Vesely |
| 2006/0142838 A1 | 6/2006 | Molaei et al. |
| 2006/0142848 A1 | 6/2006 | Gabbay |
| 2006/0167474 A1 | 7/2006 | Bloom et al. |
| 2006/0178740 A1* | 8/2006 | Stacchino ............ A61F 2/2436 623/2.18 |
| 2006/0190017 A1 | 8/2006 | Cyr et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0229659 A1 | 10/2006 | Gifford et al. |
| 2006/0241656 A1 | 10/2006 | Starksen et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271081 A1 | 11/2006 | Realyvasquez |
| 2006/0271166 A1 | 11/2006 | Thill et al. |
| 2006/0271175 A1 | 11/2006 | Woolfson et al. |
| 2006/0276775 A1 | 12/2006 | Rosenberg et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010850 A1 | 1/2007 | Balgobin et al. |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0055357 A1 | 3/2007 | Pokorney et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck-Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100302 A1 | 5/2007 | Dicarlo et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112355 A1 | 5/2007 | Salahieh et al. |
| 2007/0112415 A1 | 5/2007 | Bartlett |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0118215 A1 | 5/2007 | Moaddeb |
| 2007/0142968 A1 | 6/2007 | Prisco et al. |

(56) References Cited

U.S. PATENT DOCUMENTS

| | | |
|---|---|---|
| 2007/0156225 A1 | 7/2007 | George et al. |
| 2007/0162100 A1 | 7/2007 | Gabbay |
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0213838 A1 | 9/2007 | Hengelmolen |
| 2007/0219630 A1 | 9/2007 | Chu |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250097 A1 | 10/2007 | Weitzner et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0265702 A1 | 11/2007 | Lattouf |
| 2007/0270944 A1 | 11/2007 | Bergheim et al. |
| 2007/0288000 A1 | 12/2007 | Bonan |
| 2007/0288089 A1 | 12/2007 | Gurskis et al. |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0048656 A1 | 2/2008 | Tan et al. |
| 2008/0065001 A1 | 3/2008 | Dinucci et al. |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0102439 A1 | 5/2008 | Tian et al. |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183097 A1 | 7/2008 | Leyde et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0208216 A1 | 8/2008 | Cerier |
| 2008/0208327 A1 | 8/2008 | Rowe |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1* | 10/2008 | Stacchino ............ A61F 2/2418 623/2.11 |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262507 A1 | 10/2008 | Righini et al. |
| 2008/0262593 A1 | 10/2008 | Ryan et al. |
| 2008/0262603 A1 | 10/2008 | Giaquinta et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Sun et al. |
| 2009/0069890 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0105794 A1 | 4/2009 | Ziarno et al. |
| 2009/0118580 A1 | 5/2009 | Sun et al. |
| 2009/0125098 A1 | 5/2009 | Chuter |
| 2009/0138079 A1 | 5/2009 | Tuval et al. |
| 2009/0157174 A1 | 6/2009 | Yoganathan et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171447 A1 | 7/2009 | Von Segesser et al. |
| 2009/0171456 A1 | 7/2009 | Kveen et al. |
| 2009/0177275 A1 | 7/2009 | Case |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192602 A1 | 7/2009 | Kuehn |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210025 A1 | 8/2009 | Ameri |
| 2009/0210052 A1 | 8/2009 | Forster et al. |
| 2009/0216310 A1* | 8/2009 | Straubinger .......... A61F 2/2418 623/1.26 |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0228093 A1 | 9/2009 | Taylor et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0240326 A1 | 9/2009 | Wilson et al. |
| 2009/0248149 A1 | 10/2009 | Gabbay |
| 2009/0254165 A1 | 10/2009 | Tabor et al. |
| 2009/0276040 A1 | 11/2009 | Rowe et al. |
| 2009/0281609 A1 | 11/2009 | Benichou et al. |

(56) References Cited

U.S. PATENT DOCUMENTS

| | | |
|---|---|---|
| 2009/0281619 A1 | 11/2009 | Le et al. |
| 2009/0287296 A1* | 11/2009 | Manasse ............... A61F 2/2418 623/1.26 |
| 2009/0287299 A1 | 11/2009 | Tabor et al. |
| 2010/0004739 A1 | 1/2010 | Vesely |
| 2010/0004740 A1 | 1/2010 | Seguin et al. |
| 2010/0030328 A1 | 2/2010 | Seguin et al. |
| 2010/0030340 A1 | 2/2010 | Wolfinbarger, Jr. et al. |
| 2010/0036479 A1 | 2/2010 | Hill et al. |
| 2010/0036485 A1 | 2/2010 | Seguin |
| 2010/0049303 A1 | 2/2010 | Guyenot et al. |
| 2010/0049313 A1 | 2/2010 | Alon et al. |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0145440 A1 | 6/2010 | Keranen |
| 2010/0152840 A1 | 6/2010 | Seguin et al. |
| 2010/0161045 A1* | 6/2010 | Righini ............... A61F 2/2427 623/2.18 |
| 2010/0174363 A1 | 7/2010 | Castro |
| 2010/0191326 A1 | 7/2010 | Alkhatib |
| 2010/0198346 A1 | 8/2010 | Keogh et al. |
| 2010/0204781 A1* | 8/2010 | Alkhatib ............... A61F 2/2445 623/1.26 |
| 2010/0234940 A1 | 9/2010 | Dolan |
| 2010/0249661 A1 | 9/2010 | Righini et al. |
| 2010/0256723 A1 | 10/2010 | Murray |
| 2010/0256741 A1 | 10/2010 | Hansen |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2010/0292783 A1 | 11/2010 | Giannetti et al. |
| 2010/0292784 A1 | 11/2010 | Giannetti et al. |
| 2010/0312333 A1 | 12/2010 | Navia et al. |
| 2011/0029072 A1 | 2/2011 | Gabbay |
| 2011/0071624 A1 | 3/2011 | Finch et al. |
| 2011/0082539 A1 | 4/2011 | Suri |
| 2011/0098800 A1 | 4/2011 | Braido et al. |
| 2011/0137397 A1 | 6/2011 | Chau et al. |
| 2011/0166636 A1 | 7/2011 | Rowe |
| 2011/0178597 A9 | 7/2011 | Navia et al. |
| 2011/0218620 A1 | 9/2011 | Meiri et al. |
| 2011/0224785 A1 | 9/2011 | Hacohen |
| 2011/0288636 A1 | 11/2011 | Rolando et al. |
| 2011/0313515 A1 | 12/2011 | Quadri et al. |
| 2012/0010697 A1 | 1/2012 | Shin et al. |
| 2012/0016464 A1 | 1/2012 | Seguin |
| 2012/0022640 A1 | 1/2012 | Gross et al. |
| 2012/0046742 A1 | 2/2012 | Tuval et al. |
| 2012/0053681 A1 | 3/2012 | Alkhatib et al. |
| 2012/0053684 A1 | 3/2012 | Righini et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0172982 A1* | 7/2012 | Stacchino ............... A61F 2/2436 623/2.17 |
| 2012/0271398 A1 | 10/2012 | Essinger et al. |
| 2012/0303116 A1 | 11/2012 | Gorman, III et al. |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0123915 A1 | 5/2013 | Giannetti et al. |
| 2013/0144381 A1 | 6/2013 | Quadri et al. |
| 2013/0172991 A1 | 7/2013 | Rolando et al. |
| 2013/0211508 A1 | 8/2013 | Lane et al. |
| 2013/0231736 A1 | 9/2013 | Essinger et al. |
| 2013/0245753 A1 | 9/2013 | Alkhatib |
| 2013/0325112 A1 | 12/2013 | Stacchino et al. |
| 2013/0345800 A1 | 12/2013 | Stacchino et al. |
| 2014/0046434 A1 | 2/2014 | Rolando et al. |
| 2014/0052243 A1 | 2/2014 | Rolando et al. |
| 2014/0052244 A1 | 2/2014 | Rolando et al. |
| 2014/0088698 A1 | 3/2014 | Roels et al. |
| 2014/0155997 A1* | 6/2014 | Braido ............... A61F 2/2409 623/2.37 |
| 2014/0350666 A1 | 11/2014 | Righini |
| 2015/0018938 A1 | 1/2015 | Von Segesser et al. |
| 2015/0134052 A1 | 5/2015 | Hariton et al. |
| 2015/0148895 A1 | 5/2015 | Stacchino et al. |
| 2016/0331525 A1* | 11/2016 | Straubinger ............... A61F 2/07 |
| 2016/0354205 A1 | 12/2016 | Essinger et al. |
| 2017/0035565 A1* | 2/2017 | Stacchino ............... A61F 2/2469 |
| 2019/0224005 A1* | 7/2019 | McDonald ............ A61F 2/2418 |
| 2021/0346153 A1 | 11/2021 | Vietmeier et al. |

FOREIGN PATENT DOCUMENTS

| | | |
|---|---|---|
| DE | 3640745 A1 | 6/1987 |
| DE | 19532846 A1 | 3/1997 |
| DE | 19546692 A1 | 6/1997 |
| DE | 29911694 U1 | 8/1999 |
| DE | 29919625 U1 | 1/2000 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 19546692 C2 | 11/2002 |
| DE | 10301026 A1 | 2/2004 |
| DE | 19857887 B4 | 5/2005 |
| DE | 102004019254 B8 | 11/2005 |
| DE | 202011000848 U1 | 6/2011 |
| EP | 0095970 A2 | 12/1983 |
| EP | 0502410 A1 | 9/1992 |
| EP | 0637454 A1 | 2/1995 |
| EP | 0592410 B1 | 10/1995 |
| EP | 0512359 B1 | 12/1996 |
| EP | 0850607 A1 | 7/1998 |
| EP | 0941716 A2 | 9/1999 |
| EP | 1049425 A1 | 11/2000 |
| EP | 1057460 A1 | 12/2000 |
| EP | 1059271 A1 | 12/2000 |
| EP | 1176913 A2 | 2/2002 |
| EP | 1214050 A1 | 6/2002 |
| EP | 0778009 B1 | 7/2002 |
| EP | 1251803 A1 | 10/2002 |
| EP | 1255510 A1 | 11/2002 |
| EP | 1335683 A2 | 8/2003 |
| EP | 1343438 A2 | 9/2003 |
| EP | 1356763 A2 | 10/2003 |
| EP | 1356793 A2 | 10/2003 |
| EP | 0852481 B1 | 2/2004 |
| EP | 1401359 A2 | 3/2004 |
| EP | 1408850 A2 | 4/2004 |
| EP | 1233731 B1 | 12/2004 |
| EP | 1259194 B1 | 2/2005 |
| EP | 1214020 B1 | 3/2005 |
| EP | 1353420 B1 | 3/2005 |
| EP | 1088529 B1 | 6/2005 |
| EP | 0955895 B1 | 8/2005 |
| EP | 1562522 A2 | 8/2005 |
| EP | 1014896 B1 | 11/2005 |
| EP | 1469797 B1 | 11/2005 |
| EP | 1600127 A2 | 11/2005 |
| EP | 1603493 A2 | 12/2005 |
| EP | 1621162 A2 | 2/2006 |
| EP | 1701668 A1 | 9/2006 |
| EP | 1600127 B1 | 11/2006 |
| EP | 1758523 A1 | 3/2007 |
| EP | 1255510 B1 | 4/2007 |
| EP | 1488735 B1 | 6/2007 |
| EP | 1143882 B1 | 6/2007 |
| EP | 1212989 B1 | 1/2008 |
| EP | 1653884 B1 | 6/2008 |
| EP | 1955643 A1 | 8/2008 |
| EP | 1978895 A2 | 10/2008 |
| EP | 1986579 A2 | 11/2008 |

(56) References Cited

FOREIGN PATENT DOCUMENTS

| | | |
|---|---|---|
| EP | 2000115 A2 | 12/2008 |
| EP | 1330213 B1 | 3/2009 |
| EP | 2055266 A2 | 5/2009 |
| EP | 2072027 A1 | 6/2009 |
| EP | 2078498 A1 | 7/2009 |
| EP | 1370201 B1 | 9/2009 |
| EP | 2133039 A1 | 12/2009 |
| EP | 2138132 A2 | 12/2009 |
| EP | 2258312 A1 | 12/2010 |
| EP | 2260796 A2 | 12/2010 |
| EP | 2260797 A2 | 12/2010 |
| EP | 2260798 A2 | 12/2010 |
| EP | 2340075 A2 | 7/2011 |
| EP | 2394673 A1 | 12/2011 |
| EP | 2476394 A1 | 7/2012 |
| EP | 2526895 A1 | 11/2012 |
| EP | 2526898 A1 | 11/2012 |
| EP | 2526899 A1 | 11/2012 |
| EP | 2529696 A1 | 12/2012 |
| EP | 2529697 A1 | 12/2012 |
| EP | 2529698 A1 | 12/2012 |
| EP | 2529699 A1 | 12/2012 |
| EP | 2537487 A1 | 12/2012 |
| EP | 2641569 A1 | 9/2013 |
| EP | 2886083 A1 | 6/2015 |
| EP | 3034014 A2 | 6/2016 |
| FR | 2783217 A1 | 3/2000 |
| FR | 2788217 A1 | 7/2000 |
| FR | 2815844 A1 | 5/2002 |
| FR | 2815844 B1 | 1/2003 |
| FR | 2828091 A1 | 2/2003 |
| GB | 2056023 A | 3/1981 |
| GB | 2083362 A | 3/1982 |
| GB | 2056023 B | 8/1983 |
| GB | 2433700 A | 7/2007 |
| GB | 2433700 B | 12/2007 |
| JP | H11332997 A | 12/1999 |
| JP | 2004154164 A | 6/2004 |
| NL | 1017275 C2 | 8/2002 |
| SU | 1271508 A1 | 11/1986 |
| WO | WO-9209247 A1 | 6/1992 |
| WO | WO-9511055 A1 | 4/1995 |
| WO | WO-9529640 A1 | 11/1995 |
| WO | WO-9639942 A1 | 12/1996 |
| WO | WO-9724989 A1 | 7/1997 |
| WO | WO-9814138 A1 | 4/1998 |
| WO | WO-9817202 A1 | 4/1998 |
| WO | WO-9829057 A1 | 7/1998 |
| WO | WO-9853761 A1 | 12/1998 |
| WO | WO-9904728 A1 | 2/1999 |
| WO | WO-9912483 A1 | 3/1999 |
| WO | WO-9913802 A1 | 3/1999 |
| WO | WO-9953864 A1 | 10/1999 |
| WO | WO-9953866 A1 | 10/1999 |
| WO | WO-9955255 A1 | 11/1999 |
| WO | WO-9956665 A1 | 11/1999 |
| WO | WO-9958082 A2 | 11/1999 |
| WO | WO-0006052 A1 | 2/2000 |
| WO | WO-9953866 A8 | 2/2000 |
| WO | WO-0018303 A1 | 4/2000 |
| WO | WO-0021464 A1 | 4/2000 |
| WO | WO-0030565 A1 | 6/2000 |
| WO | WO-0041525 A2 | 7/2000 |
| WO | WO-0041652 A1 | 7/2000 |
| WO | WO-0041852 A1 | 7/2000 |
| WO | WO-0044313 A1 | 8/2000 |
| WO | WO-0047136 A1 | 8/2000 |
| WO | WO-0047139 A1 | 8/2000 |
| WO | WO-0062714 A1 | 10/2000 |
| WO | WO-0062716 A1 | 10/2000 |
| WO | WO-0117496 A1 | 3/2001 |
| WO | WO-0121076 A1 | 3/2001 |
| WO | WO-0121097 A2 | 3/2001 |
| WO | WO-0121107 A1 | 3/2001 |
| WO | WO-0121110 A1 | 3/2001 |
| WO | WO-0121244 A1 | 3/2001 |
| WO | WO-0135870 A1 | 5/2001 |
| WO | WO-0141828 A1 | 6/2001 |
| WO | WO-0149213 A2 | 7/2001 |
| WO | WO-0154625 A1 | 8/2001 |
| WO | WO-0162189 A1 | 8/2001 |
| WO | WO-0164137 A1 | 9/2001 |
| WO | WO-0176510 A2 | 10/2001 |
| WO | WO-0211646 A1 | 2/2002 |
| WO | WO-0222054 A1 | 3/2002 |
| WO | WO-0236048 A1 | 5/2002 |
| WO | WO-0241789 A2 | 5/2002 |
| WO | WO-0247575 A2 | 6/2002 |
| WO | WO-0121110 A9 | 8/2002 |
| WO | WO-0241789 A3 | 8/2002 |
| WO | WO-0121103 A9 | 10/2002 |
| WO | WO-02076348 A1 | 10/2002 |
| WO | WO-02078348 A2 | 10/2002 |
| WO | WO-02092257 A1 | 11/2002 |
| WO | WO-0247575 A3 | 12/2002 |
| WO | WO-03003943 A2 | 1/2003 |
| WO | WO-03003949 A2 | 1/2003 |
| WO | WO-03011195 A2 | 2/2003 |
| WO | WO-03047468 A1 | 6/2003 |
| WO | WO-03003943 A3 | 11/2003 |
| WO | WO-03094797 A1 | 11/2003 |
| WO | WO-03003949 A3 | 1/2004 |
| WO | WO-2004019825 A1 | 3/2004 |
| WO | WO-2004028399 A2 | 4/2004 |
| WO | WO-2004082527 A2 | 9/2004 |
| WO | WO-2004089250 A1 | 10/2004 |
| WO | WO-2004089253 A1 | 10/2004 |
| WO | WO-2004091455 A2 | 10/2004 |
| WO | WO-2005004753 A1 | 1/2005 |
| WO | WO-2004091455 A3 | 2/2005 |
| WO | WO-2005046525 A1 | 5/2005 |
| WO | WO-2005046528 A1 | 5/2005 |
| WO | WO-2005062980 A2 | 7/2005 |
| WO | WO-2005065200 A2 | 7/2005 |
| WO | WO-2005082578 A1 | 9/2005 |
| WO | WO-2005096993 A1 | 10/2005 |
| WO | WO-2005104957 A2 | 11/2005 |
| WO | WO-2006005015 A2 | 1/2006 |
| WO | WO-2006007401 A2 | 1/2006 |
| WO | WO-2006009690 A1 | 1/2006 |
| WO | WO-2006014233 A2 | 2/2006 |
| WO | WO-2006026371 A1 | 3/2006 |
| WO | WO-2006044679 A1 | 4/2006 |
| WO | WO-2006054107 A2 | 5/2006 |
| WO | WO-2006063199 A2 | 6/2006 |
| WO | WO-2006076890 A1 | 7/2006 |
| WO | WO-2006086135 A2 | 8/2006 |
| WO | WO-2006088712 A1 | 8/2006 |
| WO | WO-2006089517 A1 | 8/2006 |
| WO | WO-2006093795 A1 | 9/2006 |
| WO | WO-2006116558 A2 | 11/2006 |
| WO | WO-2006117016 A1 | 11/2006 |
| WO | WO-2006124649 A2 | 11/2006 |
| WO | WO-2006127089 A1 | 11/2006 |
| WO | WO-2006127765 A1 | 11/2006 |
| WO | WO-2006135551 A2 | 12/2006 |
| WO | WO-2006135831 A1 | 12/2006 |
| WO | WO-2006136930 A1 | 12/2006 |
| WO | WO-2006138173 A2 | 12/2006 |
| WO | WO-2007009117 A1 | 1/2007 |
| WO | WO-2007021708 A1 | 2/2007 |
| WO | WO-2007033093 A2 | 3/2007 |
| WO | WO-2007053243 A2 | 5/2007 |
| WO | WO-2007059252 A1 | 5/2007 |
| WO | WO-2007030825 A3 | 6/2007 |
| WO | WO-2007071436 A2 | 6/2007 |
| WO | WO-2007076463 A2 | 7/2007 |
| WO | WO-2007130537 A1 | 11/2007 |
| WO | WO-2006007401 A3 | 1/2008 |
| WO | WO-0121097 A3 | 3/2008 |
| WO | WO-2008028569 A1 | 3/2008 |
| WO | WO-2008031103 A2 | 3/2008 |
| WO | WO-2008035337 A2 | 3/2008 |
| WO | WO-2008047354 A2 | 4/2008 |

(56) References Cited

FOREIGN PATENT DOCUMENTS

| | | |
|---|---|---|
| WO | WO-2008070797 A2 | 6/2008 |
| WO | WO-2008089365 A2 | 7/2008 |
| WO | WO-2008091515 A2 | 7/2008 |
| WO | WO-2008097589 A1 | 8/2008 |
| WO | WO-2008125153 A1 | 10/2008 |
| WO | WO-2008138584 A1 | 11/2008 |
| WO | WO-2008150529 A1 | 12/2008 |
| WO | WO-2009002548 A1 | 12/2008 |
| WO | WO-2009024716 A2 | 2/2009 |
| WO | WO-2009029199 A1 | 3/2009 |
| WO | WO-2009042196 A2 | 4/2009 |
| WO | WO-2009045331 A1 | 4/2009 |
| WO | WO-2009045338 A1 | 4/2009 |
| WO | WO-2009053497 A1 | 4/2009 |
| WO | WO-2009061389 A2 | 5/2009 |
| WO | WO-2009081389 A1 | 7/2009 |
| WO | WO-2009091509 A1 | 7/2009 |
| WO | WO-2009094188 A2 | 7/2009 |
| WO | WO-2009106545 A1 | 9/2009 |
| WO | WO-2009111241 A2 | 9/2009 |
| WO | WO-2010008548 A2 | 1/2010 |
| WO | WO-2010112608 A1 | 10/2010 |
| WO | WO-2011044994 A1 | 4/2011 |
| WO | WO-2012063228 A1 | 5/2012 |
| WO | WO-2013037805 A1 | 3/2013 |
| WO | WO-2013075215 A1 | 5/2013 |
| WO | WO-2013082454 A1 | 6/2013 |
| WO | WO-2013096541 A1 | 6/2013 |
| WO | WO-2013128436 A1 | 9/2013 |
| WO | WO-2014121280 A2 | 8/2014 |
| WO | WO-2015036617 A2 | 3/2015 |
| WO | WO-2015191839 A1 | 12/2015 |
| WO | WO-2017195125 A1 | 11/2017 |
| WO | WO-2019224577 A1 | 11/2019 |
| WO | WO-2019224580 A1 | 11/2019 |
| WO | WO-2019224581 A1 | 11/2019 |
| WO | WO-2019224582 A1 | 11/2019 |

OTHER PUBLICATIONS

Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.

Bailey S.R., "Percutaneous Expandable Prosthetic Valves," Textbook of Interventional Cardiology, Second Edition, W.B. Saunders Company, 1994, vol. 2, pp. 1268-1276.

Block P.C., et al., "Percutaneous Approaches to Valvular Heart Disease," Current Cardiology Reports, Mar. 2005, vol. 7(2), pp. 108-113.

Bonhoeffer P., et al., "Percutaneous Insertion of the Pulmonary Valve," Journal of the American College of Cardiology, May 15, 2002, vol. 39, pp. 1664-1669.

Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.

Bonhoeffer P., et al., "Transcatheter Implantation of a Bovine Valve in Pulmonary Position: A Lamb Study," Circulation, Aug. 15, 2000, vol. 102, pp. 813-816.

Boudjemline Y., et al., "Images in Cardiovascular Medicine: Percutaneous Aortic Valve Replacement in Animals," Circulation, United States, Mar. 16, 2004, vol. 109, p. e161.

Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.

Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.

Boudjemline Y., et al., "Percutaneous Aortic Valve Replacement: Will We Get There?," Heart, British Cardiac Society, England, Dec. 2001, vol. 86, pp. 705-706.

Boudjemline Y., et al., "Percutaneous Implantation of a Biological Valve in Aortic Position: Preliminary Results in a Sheep Study," European Heart Journal, Sep. 1-5, 2001, vol. 22, p. 630.

Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.

Boudjemline Y., et al., "Percutaneous Implantation of a Valve in the Descending Aorta in Lambs," European Heart Journal, Jul. 2002, vol. 23, pp. 1045-1049.

Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.

Boudjemline Y., et al., "Percutaneous Valve Insertion: A New Approach?," Journal of Thoracic and Cardiovascular Surgery, United States, Mar. 2003, vol. 125(3), pp. 741-742.

Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.

Boudjemline Y., et al., "Steps Toward Percutaneous Aortic Valve Replacement," Circulation, Feb. 12, 2002, vol. 105, pp. 775-778.

Boudjemline Y., et al., "The Percutaneous Implantable Heart Valve," Progress in Pediatric Cardiology, Ireland, 2001, vol. 14, pp. 89-93.

Boudjemline Y., et al., "Transcatheter Reconstruction of the Right Heart," Cardiology in the Young, England, 2003, vol. 13, pp. 308-311.

Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.

Cribier A., et al., "Percutaneous Transcatheter Implantation of an Aortic Valve Prosthesis for Calcific Aortic Stenosis: First Human Case Description," Circulation, 2002, vol. 106, pp. 3006-3008.

Davidson M.J., et al., "Percutaneous Therapies for Valvular Heart Disease," Cardiovascular Pathology, Jan. 2006, vol. 15, pp. 123-129.

Grube E., et al., "First Report on a Human Percutaneous Transluminal Implantation of a Self-Expanding Valve Prosthesis for Interventional Treatment of Aortic Valve Stenosis," Valvular Heart Disease, Catheterization and Cardiovascular Interventions, 2005, vol. 66, pp. 465-469.

Grube E., et al., "Percutaneous Implantation of the Core Valve Self-Expanding Valve Prosthesis in High-Risk Patients With Aortic Valve Disease: The Siegburg First-in-Man Study," American Heart Association, Circulation, 2006, vol. 114, pp. 1616-1624.

Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.

Ho P.C., "Percutaneous Aortic Valve Replacement: A Novel Design of the Delivery and Deployment System," Minimally Invasive Therapy, 2008, vol. 17(3), pp. 190-194.

Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.

Huber C.H., et al., "Do Valved Stents Compromise Coronary Flow?," European Journal of Cardio-thoracic Surgery, Jan. 23, 2004, vol. 25, pp. 754-759.

International Search Report and Written Opinion for International Application No. PCT/IB2018/053640, dated Feb. 12, 2019, 10 pages.

International Search Report and Written Opinion for International Application No. PCT/IB2018/053646, dated Feb. 22, 2019, 9 pages.

Khambadkone S., et al., "Nonsurgical Pulmonary Valve Replacement: Why, When, and How?," Catheterization and Cardiovascular Interventions, United States, Jul. 2004, vol. 62, pp. 401-408.

(56) References Cited

OTHER PUBLICATIONS

Khambadkone S., et al., "Percutaneous Implantation of Pulmonary Valves," Expert Review of Cardiovascular Therapy (England), Nov. 2003, vol. 1(4), pp. 541-548.

Khambadkone S., et al., "Percutaneous Pulmonary Valve Implantation: Early and Medium Term Results," Circulation, Oct. 28, 2003, vol. 108(17), p. IV-375.

Khambadkone S., et al., "Percutaneous Pulmonary Valve Implantation: Impact of Morphology on Case Selection," Circulation, Oct. 28, 2003, vol. 108(17), pp. IV-642-IV-643.

Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.

Lutter G., et al., "Percutaneous Valve Replacement: Current State and Future Prospects," Annals of Thoracic Surgery, Netherlands, Dec. 2004, vol. 78, pp. 2199-2206.

Ma L., et al., "Double-Crowned Valved Stents for Off-Pump Mitral Valve Replacement," European Journal of Cardio-Thoracic Surgery, Jun. 13, 2005, vol. 28(2), pp. 194-199.

Medtech Insight, "New Frontiers in Heart Valve Disease," Aug. 2005, vol. 7(8), 38 pages.

Palacios I.F., "Percutaneous Valve Replacement and Repair: Fiction or Reality?," Journal of American College of Cardiology, Oct. 2004, vol. 44(8), pp. 1662-1663.

Pavcnik D., et al., "Aortic and Venous Valve for Percutaneous Insertion," Minimally Invasive Therapy & Allied Technologies, Jan. 2000, vol. 9(3/4), pp. 287-292.

Pelton A.R., et al., "Medical Uses of Nitinol," Materials Science Forum, Jan. 2000, vol. 327-328, pp. 63-70.

Roth M., "Old Metal Heart Valve Did its Job for 42 Years," Pittsburgh Post-Gazette, Mar. 5, 2008, 3 pages.

Ruiz C.E., "Transcatheter Aortic Valve Implantation and Mitral Valve Repair: State of the Art," Pediatric Cardiology, Jun. 2005, vol. 26(3), pp. 289-294.

Saliba Z., et al., "Treatment of Obstructions of Prosthetic Conduits by Percutaneous Implantation of Stents," Archives Des Maladies Du Coeur Et Des Vaisseaux, May 1999, pp. 591-596.

Stassano P., et al., "Mid-term Results of the Valve-on-Valve Technique for Bioprosthetic Failure," European Journal of Cardiothoracic Surgery, Oct. 2000, vol. 18, pp. 453-457.

Webb J.G., et al., "Percutaneous Aortic Valve Implantation Retrograde from the Femoral Artery," Circulation, American Heart Association, Feb. 14, 2006, vol. 113, pp. 842-850.

\* cited by examiner

CARDIAC VALVE PROSTHESIS

CROSS-REFERENCE TO RELATED APPLICATIONS

This application is a divisional of U.S. patent application Ser. No. 17/056,382, filed Nov. 17, 2020, now U.S. Pat. No. 11,504,231, which is a national stage application of PCT/IB2018/053640, filed May 23, 2018, the entire contents of each of which are incorporated herein by reference.

FIELD OF THE DISCLOSURE

The present disclosure relates to cardiac valve prosthesis. More specifically, the disclosure has been developed with reference to so-called "stented" cardiac valve prostheses, i.e. featuring a support structure and a prosthetic heart valve carried by the support structure, wherein the support structure is generally referred to as "armature" and is provided as a stent member.

BACKGROUND

Some cardiac valve prostheses include a multi leaflet prosthetic heart valve sutured, stitched, or otherwise permanently connected to the armature, which defines a lumen for the passage of blood through the prosthesis. The armature is provided as a stent member, and as such it exhibits extensive deformation capabilities. Typically, an armature of a stented cardiac valve prosthesis features a radially collapsed configuration intended for delivery and positioning of the same to and at the implantation site (for example via a delivery instrument such as a catheter), and a radially expanded configuration which is intended to ensure that the prosthesis is withheld at the implantation site once implanted.

Sometimes, the prosthetic valve includes a set of prosthetic valve leaflets supported by the armature and configured to move, under the action of blood flow, in a radially divaricated condition to enable the flow of blood through the lumen in a first direction, and in a radially contracted condition, in which the valve leaflets co-operate with one another (so-called leaflet coaptation) and block the flow of blood through the prosthesis in the direction opposite said first direction.

As the prosthetic valve is coupled to the armature, there is a certain degree of structural interaction between the same, which results in the operation of the prosthetic valve being possibly affected by the structural condition the armature experiences at the end of the implantation procedure, with the valve sitting at the implantation site. The shape of the implantation site (the valve annulus) may affect the in vivo functionality of the valve. For example, a D-shaped annulus may encourage leaflet straightening, which in turn may end up with negatively affecting leaflet coaptation. This happens generally because the irregular shape of the annulus, meaning by this a deviation from the ideal circular shape. As a D-shaped annulus may notionally be regarded as a "flattened" circular annulus, the armature of the prosthesis will experience an irregular deformation pattern over the perimeter of the annulus, and especially over the "flattened" portion. This may result in a sensible change, for example, in relative position of support posts of the armature to which the prosthetic valve is attached, and especially an increase in the mutual distance between two supporting posts possibly located at the "flattened" side. Such an increase in distance causes the leaflet straightening referred to above, which in turn is susceptible of encouraging regurgitation of blood through the prosthesis. This is clearly an undesirable condition, in that functionality of the native heart valve replaced by the prosthesis will not be restored, not to mention the damage that this could cause to an already suffering patient.

Additionally, radially protruding anchoring formations possibly provided on the armature of the prosthesis may affect the resistance to bending when the prosthesis is implanted at sites such as the annulus of a bicuspid valve, or a flat Valsalva Sinus. Accordingly, the prosthesis will be subject to a bending phenomenon known as "folding", which is another major source of risks and damage to the patient.

SUMMARY

In a first example, a cardiac valve prosthesis comprising an armature for anchorage of the valve prosthesis at an implantation site. The armature defining a lumen for the passage of the blood flow and having a longitudinal axis, and a set of prosthetic valve leaflets supported by said armature and configured to move, under the action of blood flow, in a radially divaricated condition to enable the flow of blood through said lumen in a first direction, and in a radially contracted condition, in which said valve leaflets co-operate with one another and block the flow of blood through the prosthesis in the direction opposite said first direction. The armature comprising an annular part and a pattern of arched struts carried by said annular part, said pattern of arched struts having proximal ends connected to said annular part, and distal ends spaced axially from the proximal ends and opposite said annular part. Where, a plurality of sets of anchoring formations configured to protrude radially outwardly of said annular part, each set being supported by at least one of said annular part and a corresponding arched strut, and a plurality of support posts, each support post being supported by adjacent arched struts. Where, the sets of anchoring formations alternate with the support posts around said longitudinal axis.

In a second example according to the first example, wherein each set of anchoring formations extends bridgewise between a corresponding arched strut and said annular part.

In a third example according to the first example or the second example, wherein each support post is cantilevered to adjacent arched struts.

In a fourth example according to any of the previous examples, wherein each arched strut extends from a first proximal end, to a distal end, and then to a second proximal end.

In a fifth example according to the fourth example, wherein each set of anchoring formations extends bridgewise from an arched strut to a portion of the annular part comprised between two proximal ends.

In a sixth example according to the fifth example, wherein each set of anchoring formations comprises two anchoring formations.

In a seventh example according to the fifth example or the sixth example, wherein each anchoring formation comprises a serpentine, a weaving, or an apertured pattern.

In an eighth example according to the fourth example, wherein each support post is angularly arranged between two adjacent arched struts at an inter-strut position, said inter-strut position corresponding to the position of a proximal end shared between said two adjacent arched struts.

In a ninth example according to the third example or the eighth example, wherein said support post is cantilevered to said pair of arched struts by way of a first and a second cantilever struts merging at the supporting post.

In a tenth example according to any of the previous examples, wherein said annular part is covered by a cuff to provide sealing at the implantation site, the cuff being arranged outside of the lumen of the armature.

In an eleventh example according to the tenth example, wherein the cuff is separate from said set of prosthetic valve leaflets.

In a twelfth example according to any of the previous examples, wherein said annular part includes one or more coupling elements configured to be engaged by valve loading or crimping facilities or instruments.

In a thirteenth example according to any of the previous examples, wherein said set of prosthetic valve leaflets define a prosthetic aortic valve, the cardiac valve prosthesis being an aortic valve prosthesis.

In a fourteenth example according to the first example, wherein each arched strut includes a distal portion at the distal end thereof which is substantially C-shaped and is configured to mate with a valve holder or a carrier portion of a delivery instrument.

In a fifteenth example according to the first example or the fourteenth, wherein the pattern of arched struts includes inter-strut portions arranged at said proximal ends, and said annular part has a mesh structures including cells and nodes, said inter strut portions having a Y-shape or a U-shape extending through nodes of the mesh of the annular part.

In a sixteenth example, a cardiac valve prosthesis comprising:
  an armature for the valve prosthesis at an implantation site,
  a set of prosthetic valve leaflets supported by said armature,
  the armature comprising:
  an annular part
  a plurality of arched struts coupled to said annular part,
  a plurality of support posts each having a free proximal end and a distal portion supported by adjacent arched struts.

In a seventeenth example according to the sixteenth example, further including a plurality of sets of anchoring formations configured to protrude radially outwardly of said annular part, each set being supported by at least one of said annular part and a corresponding arched strut.

In an eighteenth example according to the sixteenth example, the support posts are cantilevered to adjacent arched struts.

In a nineteenth example according to the seventeenth example, each set of anchoring formations extends bridgewise between a corresponding arched strut and said annular part.

In a twentieth example according to the seventeenth example the sets of anchoring formations alternate with the support posts around a longitudinal axis of the prosthesis.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE FIGURES

Further features and advantages of the disclosure will become apparent from the following description with reference to the annexed drawings, given purely by way of non-limiting example, in which.

Figure 1A:
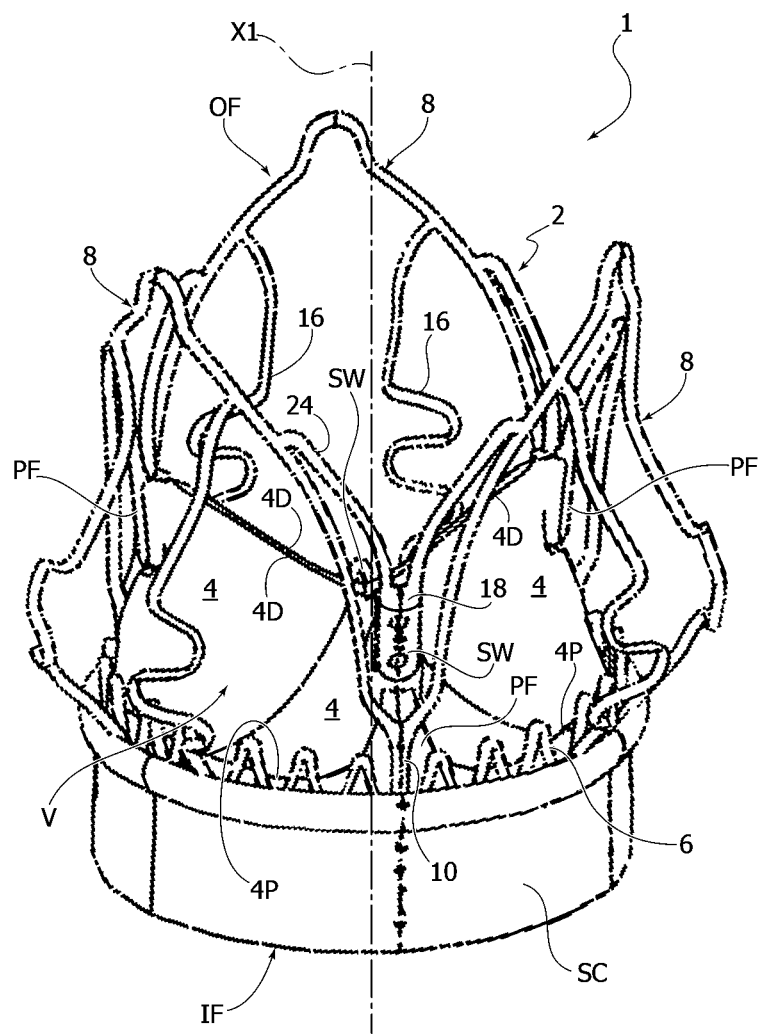
FIG. 1A is a perspective view of a cardiac valve prosthesis, according to embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION OF EMBODIMENTS

With reference to FIG. 1A, reference number 1 designates as a whole a cardiac valve prosthesis according to various embodiments of the disclosure. The cardiac valve prosthesis 1 includes an armature 2 for anchorage of the valve prosthesis at an implantation site. The armature 2 defines a lumen for the passage of the blood flow and has a longitudinal axis X1.

The prosthesis 1 also includes a set of prosthetic valve leaflets 4 supported by the armature 2 and configured to move, under the action of blood flow (which has a main flow direction roughly corresponding to that of the axis X1): in a radially divaricated condition to enable the flow of blood through the lumen in a first direction, and in a radially contracted condition, in which the valve leaflets 4 co-operate with one another and block the flow of blood through the prosthesis 1 in the direction opposite the first direction. This is commonly referred to as leaflet coaptation.

With reference to FIGS. 2-5, in embodiments the armature 2 includes an annular part 6, and a pattern of arched struts 8 carried by the annular part 6. The annular part has a structure which can expand from a radially contracted condition, associated to delivery of the prosthesis to implantation site, to a radially expanded condition wherein the prosthesis is withheld at the implantation site. In these embodiments, the annular part may have a mesh structure including an annular pattern of multiple strut clusters (cells) having polygonal shape (hexagonal, rhomboidal, etc.).

Figure 1B:
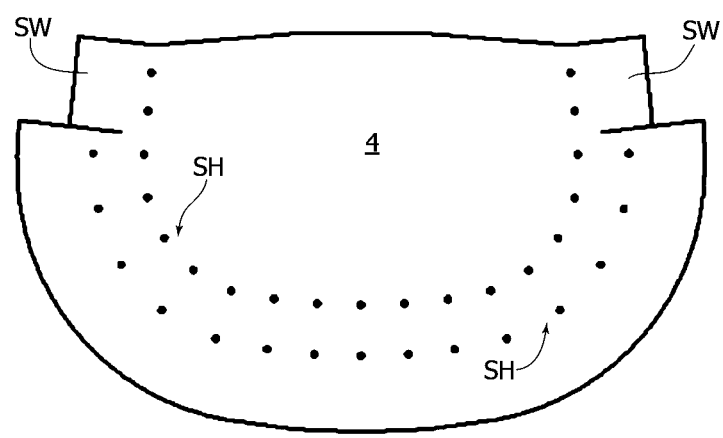
FIGS. 1B and 1C illustrate examples of trimmed portions of leaflet forming members, according to embodiments of the disclosure.

As regards the construction of the set of leaflets 4 (also referred to as or valve sleeve), in various embodiments the prosthetic valve is made with three separate leaflets. Each leaflet is obtained from one sheet of pericardium trimmed accordingly to FIG. 1B, i.e., according to a substantially lobe-shaped figure. Each trimmed leaflet features two patterns of sewing holes SH and two side wings SW.

The patterns SH are sewn together forming a sewn stiffer fold which follows the leaflet profile at the root thereof, thereby forming the cusp.

The two side wings SW enable connection of the valve to supporting posts in the valve armature. The sewn fold has the purpose to bias the cusp inwardly thereby encouraging leaflet coaptation, and to avoid contact between the armature 2 and the valve leaflets 4 avoiding the risk of abrasion due to repeated impact against the armature 2, which, in some embodiments, is a metal material.

The two patterns of holes SH may be sewn together using a suture thread coated with a film of biocompatible material or PET thread or PTFE filament.

The sewing pattern may be varied to accommodate the directional differences in the forces exerted at each point of the stitches, prevent the stitches from triggering fatigue fracture lines.

Figure 1C:
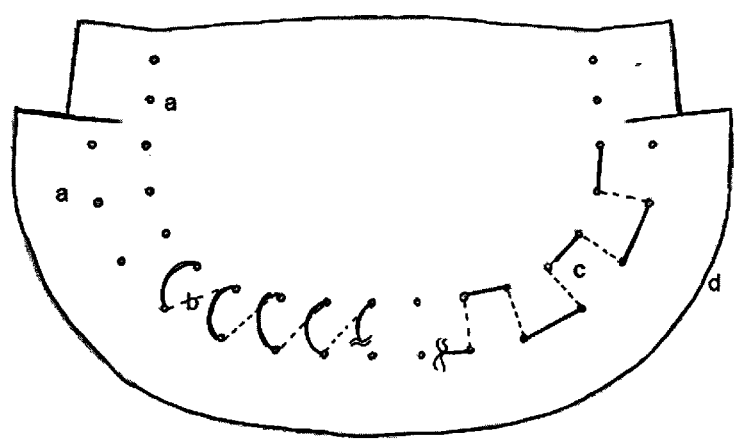
Figure 2:
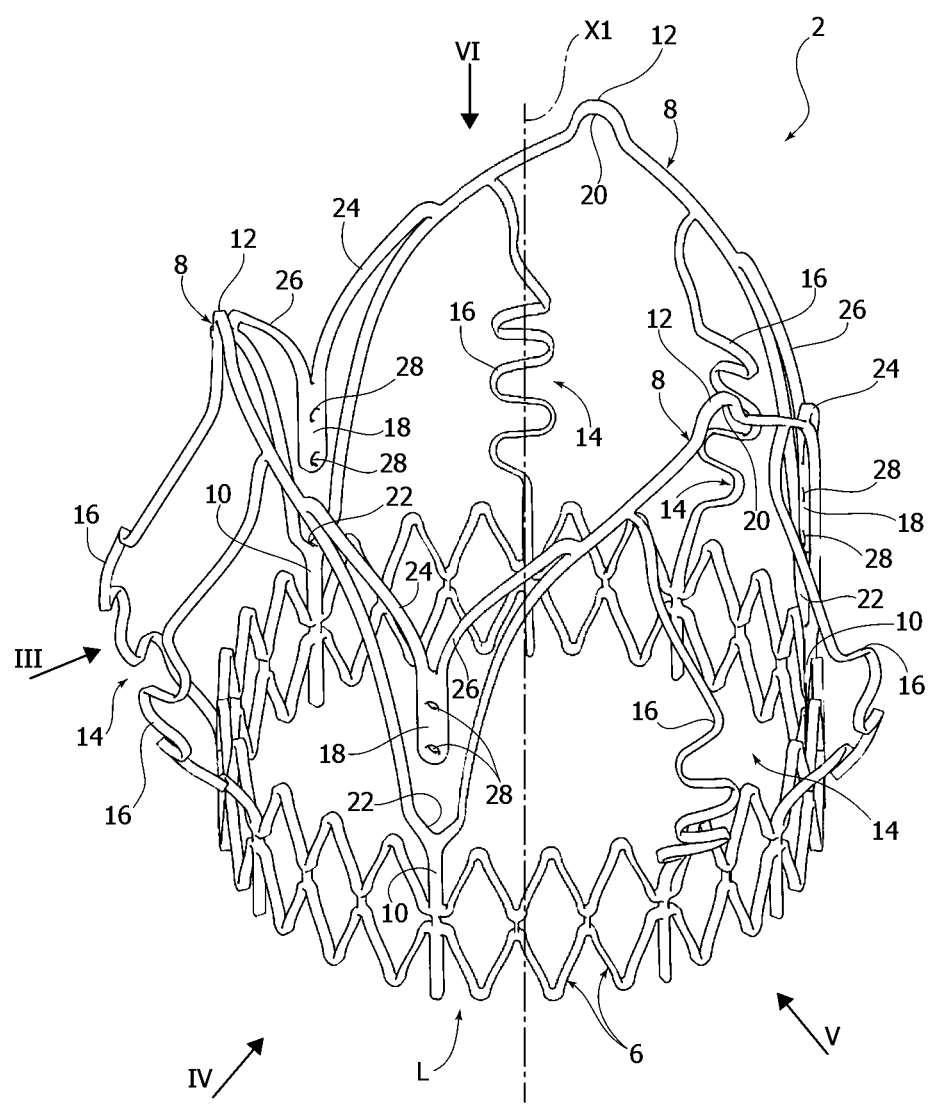
FIG. 2 is a perspective view of an armature of the prosthesis of FIG. 1, according to embodiments of the disclosure.
Figure 3:
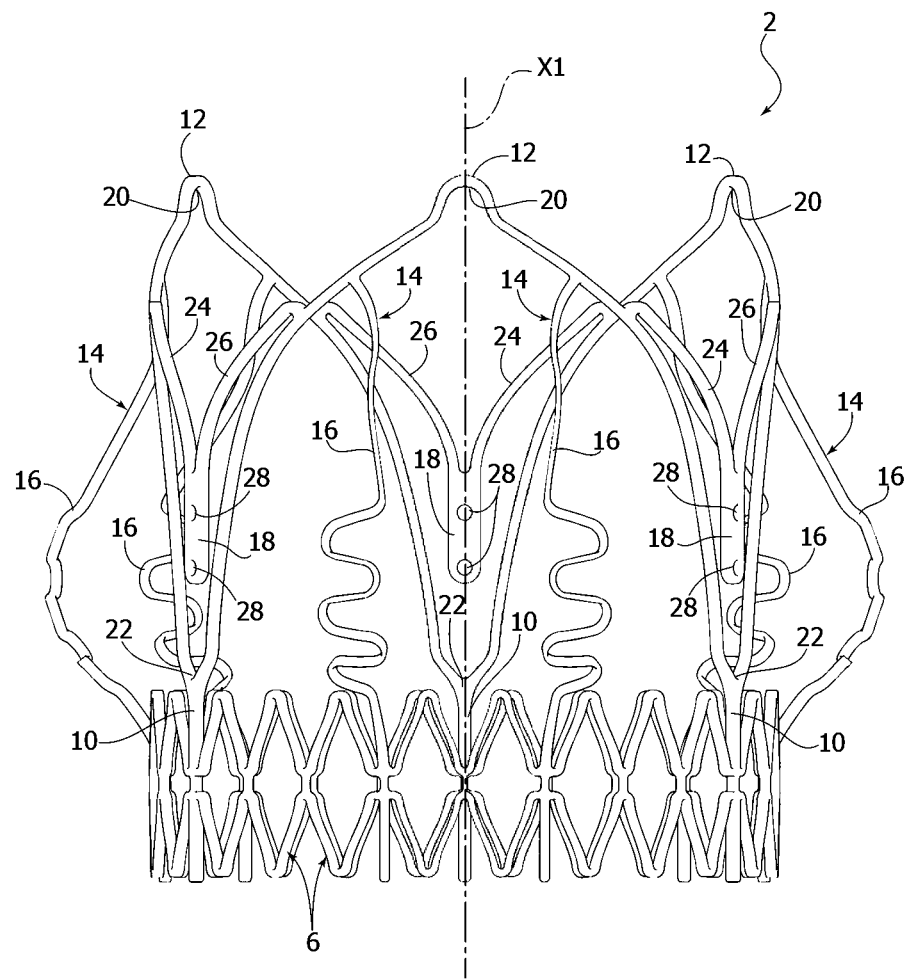
FIG. 3 is an orthogonal view of the armature of FIG. 2 according to III in FIG. 2, according to embodiments of the disclosure.
Figure 4:
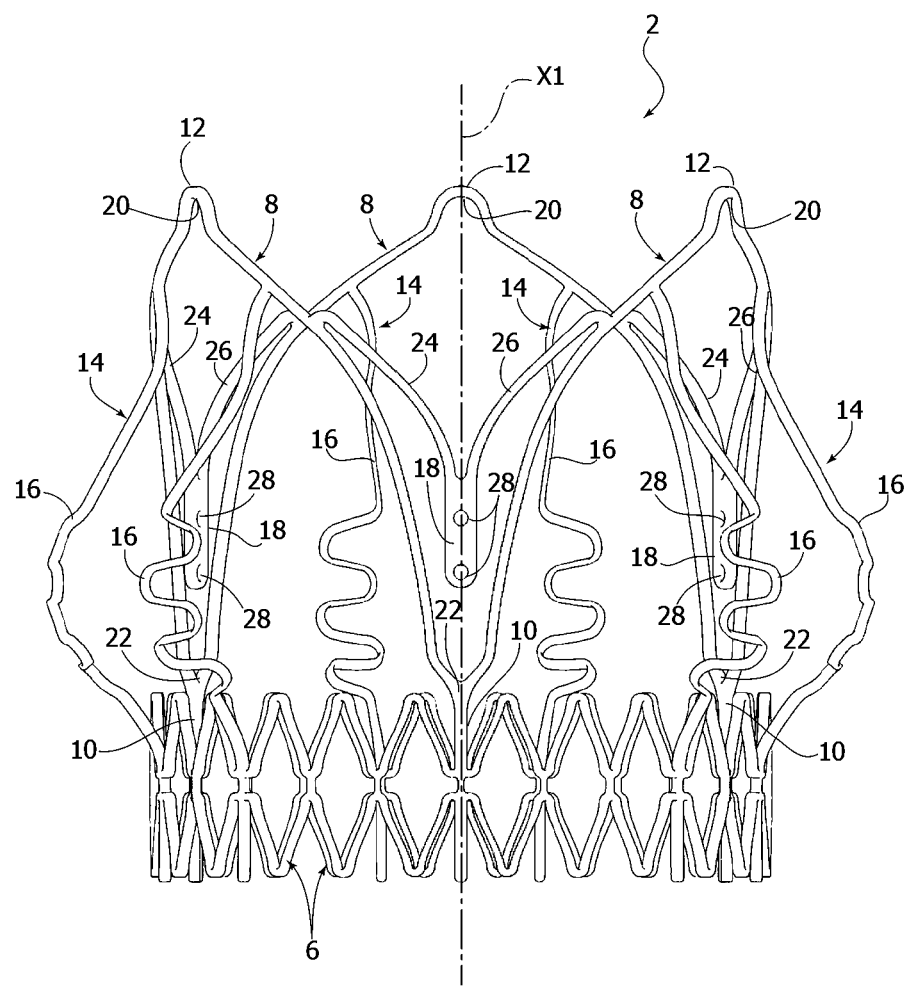
FIG. 4 is another orthogonal view of the armature of FIG. 2 according to IV in FIG. 2, according to embodiments of the disclosure.

Preferably the stitching follows the pattern identified by letter "C" in FIG. 1C (alternate inner and outer surface stitches). The three leaflets 4 are then joined at the side wings SW and stitched together along the leaflet post line, i.e., at the interface of adjacent side wings SW, thereby forming a conical duct.

The side wings SW, which allow a slack of material that protrudes outwardly of the duct, are then fixed to the armature posts, which are fully wrapped by the side wings SW.

The extra tissue skirt below the stitching holes SH allows leaflet fixation to the inflow ring 6 of the stent, by mean of a stitching line. Additionally, in some embodiments one—preferably the lower one or both of the patterns SH may be stitched to the armature at the annular part 6.

A strip of pericardium is finally stitched to the inflow ring 6 outwardly of the same, defining the sealing cuff SC. The strip can be folded on its outflow end to provide a sealing collar along the valve perimeter, or a second strip can be connected by means of a circumferential stitching line to the first strip, to realize a sealing circumferential collar.

The prosthetic leaflets 4 may be in any number compatible with operation as replacement heart valve. In some embodiments, the set includes a pair of leaflets. In some embodiments, such as that shown in the figures, the set includes three prosthetic valve leaflets 4 (e.g. for an aortic valve prosthesis). In some embodiments, the set may include four leaflets 4.

In embodiments, the leaflets 4 can be made of biological material such as, for instance, bovine or porcine pericardium. In other embodiments, the leaflets 4 can be made of non-biological material such as a non-biological woven or nonwoven fabric that exhibits hemocompatibility properties. An example of this is disclosed, for instance in EP application no. EP 16745505.4.

Each valve leaflet 4 includes a fluidodynamically proximal edge 4P with an arched pattern, which extends from a base portion at the upper pattern SH and along two adjacent pleat formations PF, and a fluidodynamically distal edge 4D which extends towards the central orifice of the prosthesis 1 so as to be able to co-operate with the homologous edges of the other valve leaflets 4.

The terms "fluidodynamically proximal" and "fluidodynamically distal" as used herein refer to the free flow direction of the blood through the prosthesis, a direction that is bottom up as viewed in the figures of the annexed plate of drawings.

During operation (heart cycle) the valve leaflets 4 experience deformation, divaricating and moving up towards the armature 2 so as to enable free flow of the blood through the prosthesis.

When the pressure gradient, and hence the direction of flow, of the blood through the prosthesis tends to be reversed, the valve leaflets 4 then move into the position represented in FIG. 1A, in which they prevent the back flow of the blood through the prosthesis.

The prosthetic valve including the valve leaflets 4 can be, for example, a glutaraldehyde fixed pericardium valve which has three cusps that open distally to permit unidirectional blood flow.

The pattern of arched struts 8 includes proximal ends 10 connected to the annular part 6, and distal ends 12 spaced axially from the proximal ends 10 and arranged at an end of the armature 2 opposite the annular part 6. In embodiments, the distal ends 12 coincide with distal ends of the armature 2, and in embodiments where the distal end of the armature 2 coincides with a distal end of the prosthesis 1 as a whole, the distal ends 12 coincide with a distal end of the prosthesis as well (this is the case of at least some of the embodiments depicted in the figures).

Owing to this layout, in embodiments, the prosthesis 1 includes an inflow portion IF essentially corresponding to the annular part 6 (whether or not covered by the sealing cuff SC), and an outflow portion OF corresponding essentially to the distal region of the armature, i.e. that where the distal ends 12 are arranged.

The armature 2 further includes a plurality of sets 14 of anchoring formations 16 configured to protrude radially outwardly of the annular part 6, each set 14 being supported by at least one of the annular part 6 and a corresponding arched strut 8, and a plurality of support posts 18, each supported by adjacent arched struts 8, wherein the sets 14 of anchoring formations 16 alternate with the support posts 18 around the longitudinal axis X1. In embodiments the support posts 18 are advantageously cantilevered to adjacent arched struts 8 and are configured as fixing locations for the prosthetic valve, specifically for the pleat formations PF at the commissural points of the valve. In this regard, the posts 18 are wrapped by adjacent side wings SW previously stitched together during assembly of the prosthetic valve.

Figure 5:
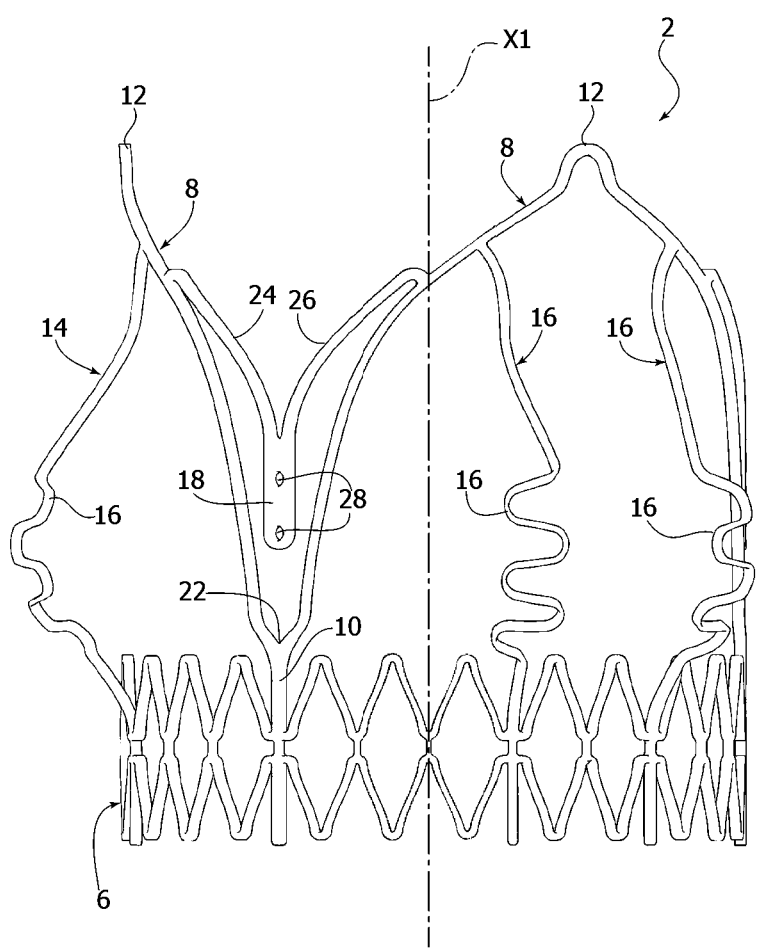
FIG. 5 is a further orthogonal view of the armature of FIG. 2 according to V in FIG. 2, according to embodiments of the disclosure.
Figure 6:
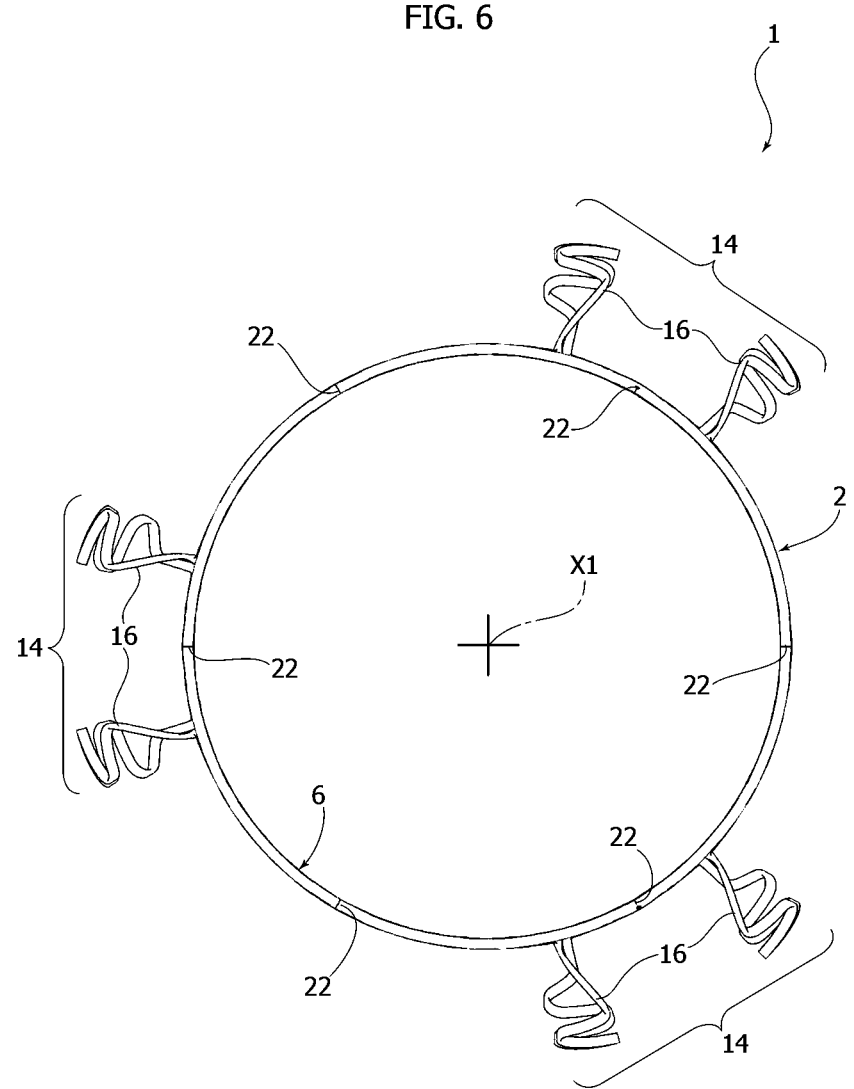
FIG. 6 is yet a further orthogonal view of the armature of FIG. 2 according to VI in FIG. 2, according to embodiments of the disclosure.

Referring again to FIGS. 2-5, in embodiments each arched strut 8 extends from a first proximal end 10, to a distal end 12, then to a second proximal end 10 in a valley-peak-valley sequence, wherein valleys are located at the proximal ends 10, and peaks are located at the distal ends 12. In embodiments the pattern of arched struts includes three adjacent and preferably identical arched struts 8 (such as in the figures). With reference to FIG. 5 and FIG. 6, in embodiments, the arched struts 8 extend within the boundaries of the inner and outer surfaces of the armature 2, so as to be substantially free of any protrusion relative to those surfaces. In other embodiments the arched struts may have an offset from the inner and outer surfaces of the armature 2, meaning by this they may either protrude radially inwardly or radially outwardly of two cylinder surfaces tangent to the inner and outer surfaces of the armature 2 (in the view of FIG. 6, this would correspond to a radially inward or a radially outward offset from the circular perimeter of the lumen defined by the armature 2.

In embodiments, the arched struts are sized and dimensioned so as to have a variable curvature between a proximal end 10 and a distal end 12, for example with the arched shape starting with a 45 degrees tangent at the proximal end 10, and ending up with an 80 degrees tangent at the distal end, the angle being measured relative to a direction parallel to the axis X1

In some embodiments, the arched struts 8 are sized and dimensioned so as to exhibit appreciable variations in curvature between proximal and distal ends 10, 12. The pattern of arched struts 8 includes distal portions 20 located at the distal ends 12, and inter-strut portions 22 located at the proximal ends 10. The distal portions 20 may be shaped so as to provide a marked local variation in the shape of the strut, for example by exhibiting a C-shape as shown in the figures. The distal portions 20 may provide coupling locations for other devices such as a valve holder or a hub of a carrier portion of a delivery catheter. In other embodiments, the distal portions 20 may be provided as closed-loop structures such as eyes or eyelets. Note also that closed loop structures may be provided at the annular part 6 (either as part of the armature 2 or on the sealing cuff SC, for example as loops made of yarn and weaved through the cuff SC) as coupling elements intended to be engaged e.g. by valve loading or crimping facilities or instruments.

In embodiments, the inter-strut portions 22 are essentially V-shaped and are defined by the roots of the adjacent arched struts departing from the same proximal end 10. In some embodiments, the inter strut portions 22 may exhibit a Y-shape or a U-shape. An example of a Y-shape is shown in the figures (particularly FIGS. 2-5) wherein each inter-strut portion 22 extends through the mesh of the annular part 6. In these embodiments, the mesh of the annular part 6 is provided as a sequence of rhomboidal strut clusters (cells) sequentially connected to each other at endpoints of a diagonal line (such as the shortest diagonal) and exhibiting accordingly an identical circular pattern of free ends on opposite sides of a circumference extending through the sequence of the connection points. The Y-shaped inter-strut portion 22 is thus integrally formed at a selected connection point between two adjacent rhomboidal strut clusters, and may extend no further than the proximal end of the armature 2.

In embodiments the strut clusters may be arranged according to an arrow shape, i.e. defined by two axially staggered sinusoidal patterns, circumferentially in phase, bridged by longitudinal struts.

In embodiments, the support posts 18 are angularly arranged at an inter-strut location, i.e., a circumferential location arranged at an area where an inter-strut portion 22 (as well as accordingly a proximal end 10 shared by two adjacent arched struts 8) is provided. The support posts may be provided as cantilevered to both the adjacent arched struts 8 intervening at an inter-strut portion 22 via a first and a second cantilever struts 24, 26, each connected to a corresponding one of said adjacent arched struts 8 as shown in the figures. In some embodiments, each cantilever strut 24, 26 may be a twin strut.

The cantilever struts 24, 26 merge into each corresponding post 18 starting from locations on respective arched strut 8 approximately halfway through the portion of the arched strut 8 extending from a proximal end 10 to a distal end 12. Note that in other embodiments the support posts 18 may be cantilevered to the annular part 6, for example by being formed integrally with the inter-strut portion 22 (which in this case will exhibit a trident shape).

The connection points at which the Y-shaped inter-strut portion 22 is formed may be chosen so that the same portions are evenly spaced (angular-wise) around the axis X1. The same applies to the support posts 18, which may be arranged so as to be evenly spaced (angular-wise) around the axis X1.

In some embodiments shown in the figures, the armature 2 comprises three arched struts 8, three posts 18 spaced 120° around the axis X1, and three sets 14, so that the sequence around the axis X1 is post 18-set 14-post 18-set 14-post 18-set 14 (in this sense, even the struts 8 and the sets 14 do follow a 120 degree-like distribution). In embodiments the three sets 14 include each a pair of anchoring formations 16, wherein each set 14 (and accordingly each anchoring formation 16) extends bridge-wise between the annular part 6 and the corresponding arched strut 8. In embodiments, each pair of anchoring formations 16 extend bridge wise at an intra-strut location, that is a location within an arched strut 8 and as such comprised between two proximal ends 10 of the same arched strut 8 and under a distal end 12/distal portion 20. In other words, each set 14 of anchoring formations 16 extends bridge-wise from the arched strut 8 to a portion of the annular part 6 comprised between two proximal ends 10.

The support posts 18, accordingly, are arranged at an inter-strut location (e.g. above the inter-strut portion 22 as shown in the figures) so that the sequence post 18-set 14-post 18-set 14-post 18-set 14 is provided, location-wise, as inter-strut-intra-strut-inter-strut-intra-strut-inter-strut-intra-strut.

In embodiments, the support posts 18 are provided with bores 28 configured for receiving sutures or stitches that fix the commissural portions (pleat formations of the valvular sleeve) to the posts 18, hence fixing the prosthetic valve to the armature 2. In some embodiments, the prosthetic valve is fixed to the support posts 18 with the same being completely outside of the valve. Sutures or stitches are routed through the bores 28 and through the valve layers contacting the corresponding post 18 from inside of the lumen. In other embodiments, the posts 18 may be wrapped by the valve layers—particularly by the commissural points of the valve—so that the valve is at least partially "outside" of the posts 18.

In embodiments, the anchoring formations may include a serpentine or otherwise weaving portion between opposite ends thereof. Such a serpentine or otherwise weaving portion is intended to provide a larger footprint to the anchoring formation at the interface with a Valsalva Sinus, and additionally it enables the bulging of the anchoring formations to a diameter larger than the inflow diameter, typically 1.4 or 1.5 times the inflow diameter.

The prosthesis 1 shown in FIG. 1A is particularly suitable as aortic valve prosthesis, i.e. for replacement of an aortic valve. To this end, the prosthetic valve includes three identical leaflets 4 and the armature 2 is designed as a whole—as described above—according to 120°—spacing (or, where appropriate, a ⅓ coverage) criteria: three posts 18 at 120° apart, three sets 14 evenly distributed around the axis X1, and three arched struts 8 covering approximately one third of the circumferential extension of the annular part 6.

Figure 7:
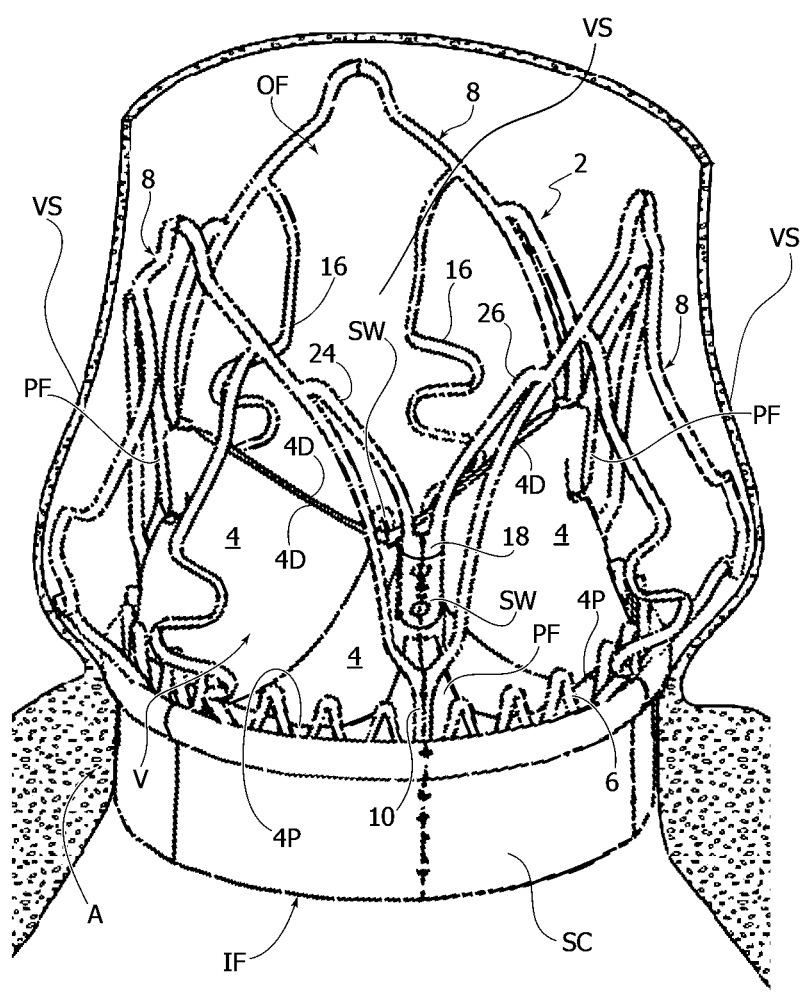
FIG. 7 is exemplary of an implantation of the heart valve prosthesis, according to embodiments of the disclosure.

The prosthesis 1 may be implanted as shown in FIG. 7, so that the inflow portion IF at the annular part 6 occupies a proximal position relative to the Valsalva sinus VS, including a native valve annulus, while the anchoring formations 16 extend into the lobes of the Valsalva sinus VS (one set 14 per each Sinus) to firmly anchor the prosthesis 1 in place. The pattern of arched struts 8 is configured to follow the contour of the Valsalva Sinus at the interface with the ascending aorta, distally of the Sinus itself. The distal portions 20 of the distal ends 12 in various embodiments are intended to sit just distally of the Sinus.

In embodiments, achieving this placement of the prosthesis 1 may include sizing and dimensioning the prosthesis according to the following specifications (all endpoints included in the ranges):

axial length of the annular part 6 (inflow portion IF): 7 to 10 mm;

total axial length of the prosthesis (e.g. measured from a proximal end of the inflow portion If to the distal portions 20): 25 to 37 mm;

expanded diameter of the inflow portion IF (outer diameter of annular part 6, including sealing collar SC: 23 to 33 mm; and extended outer diameter of anchoring formations 16, measured at the most radially outward portion of the anchoring formations: 31 to 44 mm.

Additionally, the prosthetic valve carried by the armature 2 may be sized and dimensioned according to the following specifications:

ventricular protrusion: 5 to 8 mm; and
implantation diameter: 19 to 29 mm.

The paired anchoring formations 16—especially when provided with a serpentine or otherwise weaving pattern as shown in the figures—favourably contact the Sinus to hold the prosthesis 1 in place by bulging radially outwardly of the armature 2. The anchoring formations 16 of each pair may advantageously be positioned on opposite sides of the coronary ostia in the respective sinuses of Valsalva, with the serpentine or otherwise generally weaving (or else aperture) structure thereof substantially avoiding interference with the coronary ostia.

The armature 2 of the prosthesis 1, according to embodiments, is manufactured by first cutting a blank part from a tube of a biocompatible metal (e.g., Nitinol, or a cobaltum-chromium alloy) having an outer diameter which is at an intermediate size between the fully radially contracted and the fully expanded device dimensions. For example, the tube may have an outer diameter of between about 10 mm to about 14 mm. In some embodiments, the tube has a diameter of about 12 mm. In some embodiments, the tube wall may vary between about 0.4 mm to about 0.6 mm, depending on the required stiffness required and the size of the prosthesis 1.

In embodiments, the final dimension and shape of the framework is achieved by a sequence of expansion cycles. A specific heat treatment is applied after each expansion cycle to homogenize and stress relieve the material, which allows the shape and properties of the structure of the armature 2 to be set. Although the number of forming steps may vary among devices, for the geometries described above with respect to the present disclosure, and using Nitinol for the tube blank, an exemplary number of forming steps is around three. Among these steps, the first two provide the final diameter of the annular part 6. For example, if the fully-expanded diameter for implantation is 20.5 mm, the final cylindrical shape of the armature 2 can be achieved using a tube blank of about 12 mm in inner diameter, a first expansion from about 12 mm to about 15 mm, and a second expansion from about 15 mm to about 19.5 and a third expansion from about 19.5 to 21.5 mm. Optionally, the final diameter can be made slightly larger (e.g. about 21.5 mm in the previous example) in order to oversize the armature 2 with respect to the physiological annulus, thus imparting a radial force to the wall of the annulus at the nominal implant diameter.

All the forming steps are also aimed to impart the radially-extending shape of the anchoring formations 16 such that they will fit and anchor within the Valsalva sinuses.

After the forming process is complete, the armature 2 may undergo one or more surface treatments, for example, sand-blasting and electropolishing, to provide a sufficiently smooth surface and to remove the shallow defects. The armature 2 may thereafter be finally exposed to a carbon coating process in order to improve its hemocompatibility.

The final geometrical shape of the armature 2 will thus generally approximate the physiological shape and dimension of the aortic root, such that the anchoring formations 16 generally conform to the walls of the respective Valsalva sinuses VS.

The prosthesis 1 is delivered to the implantation site in a radially contracted condition, for example crimped and loaded into a delivery instrument such as a catheter. The prosthesis may be implanted using minimally invasive techniques or via conventional surgical techniques such as sternotomy or thoracotomy. Once on site, the prosthesis 1 is released from the catheter so to allow the annular part 6 to expand to the radially expanded configuration and the anchoring formations 16 to settle into the Valsalva Sinus.

In embodiments, the provision of support posts 18 that are cantilevered to the arched struts 8 decouples the deformation pattern of the proximal portion of the prosthesis 1—that is, the annular part 6—from the deformation pattern of the distal portion of the same prosthesis—that is, the portions of arched struts 8 converging to the distal ends 12. If the implantation site has an irregular shape (like a D-shape) such as to result in substantial alterations of leaflet functionality with prior art prostheses, the prosthesis 1 on the contrary allows the annular part to adapt to the shape of the implantation site without transmitting any of the deformations resulting therefrom to the support posts 18, which essentially maintain the advertised position on the armature 2 by remaining spaced 120 degrees apart. In the case of an aortic implantation site, the deformation pattern of the annular part 6 may be largely variable on account of the shape of the site per se, and/or the size of calcium deposits possibly present at the implantation site, while the deformation pattern of the arched struts 8 may be—instead—reasonably predictable and regular on account of a lesser variability of conditions at the locations concerned (Valsalva Sinus and ascending aorta). Therefore, the support posts 18 may take benefit from highly predictable and reasonably regular deformation of the portions of the armature it is attached to, thereby keeping the relative position thereof and allowing the prosthetic valve with the valve leaflets 4 to operate as efficiently as possible, and ultimately independently of the shape and conditions of the implantation site.

Additionally, folding phenomena of the prosthesis are avoided owing to the armature design. Folding generally occurs on account of an inward rotation of the anchoring formations 16, wherein one rotates clockwise, and the other one rotates counterclockwise to jointly result in an inward displacement of annular part 6. Anchoring formations 16 bridging two structural portions having a substantial axial extension and/or resistance to bending (relative to that of the anchoring formations) may encourage—undesirably—these pheonomena, as the anchoring formations end up with accommodating a major share of deformations within the armature 2, which the structural portions above (e.g. two annular portions at opposite ends of the armature) inherently cannot accommodate.

Because the armature 2 features the pattern of arched struts 8, the anchoring formations 16 essentially bridge one structural portion, such as the annular part 6, that has a substantial axial extension and/or resistance to bending relative to the formations 16, and another structural portion such as the arched struts 8 which is subject to a binding structural constraint primarily at the proximal portions thereof (i.e. the proximal ends 10 and the inter-strut portions 22, while the distal portions 20 at the distal ends 12 are relatively free to accommodate deformations running through the armature from the proximal—stiffer-portions thereof (e.g. the inflow). This difference in strength or biding amount of the structural constraints the arched struts 8 are subject to allows to divert away from the anchoring formations the structural actions that would otherwise tend to rotate the anchoring formations 16. Diversion may occur, for example, over the length of the arched struts and/or towards the distal ends 12 thereof.

In other words, the arched struts tend to compensate (essentially in that they have a lesser degree of constraint to the remainder of the armature) the torsional forces on the anchoring formations 16, thereby keeping the same separate from one another and the armature 2 as a whole as close as possible to the intended shape.

Naturally, while the ideas and the principles of the disclosure remains the same, the details of construction and the embodiments may widely vary with respect to what has been described and illustrated by way of example, without departing from the scope of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed:

1. A method for implanting a cardiac valve prosthesis, the method comprising:
    advancing a cardiac valve prosthesis in a contracted state to an implantation site, the cardiac valve prosthesis comprising an armature and a set of prosthetic valve leaflets supported by the armature, the armature comprising an annular part, a plurality of arched struts coupled to the annular part, a plurality of support posts supported by adjacent arched struts, and a plurality of sets of anchoring formations; and
    deploying the cardiac valve prosthesis at the implantation site such that the plurality of sets of anchoring formation protrude radially outward of the annular part, each set supported by the annular part or a corresponding arched strut or both,
    wherein each support post is angularly arranged between two adjacent arched struts at an inter-strut position, the inter-strut position corresponding to the position of a proximal end shared between the two adjacent arched struts.

2. The method of claim 1, wherein deploying the cardiac valve prosthesis comprises deploying the cardiac valve prosthesis at an aortic valve site.

3. The method of claim 1, wherein deploying the cardiac valve prosthesis comprises causing the plurality of sets of anchoring formations to protrude radially outwardly of the annular part to contact a Valsalva sinus at the implantation site to anchor the cardiac valve prosthesis.

4. The method of claim 1, wherein advancing the cardiac valve prosthesis comprises advancing the cardiac valve prosthesis that has been crimped and loaded into a delivery instrument, and
    wherein deploying the cardiac valve prosthesis comprises releasing the cardiac valve prosthesis from the delivery instrument.

5. The method of claim 4, further comprising, prior to the advancing, crimping and loading the cardiac valve prosthesis into the delivery instrument.

6. The method of claim 1, wherein advancing the cardiac valve prosthesis comprises accessing the implantation site using minimally invasive techniques.

7. The method of claim 1, further comprising, after the deploying, permitting the set of prosthetic valve leaflets to move, under the action of blood flow, to a radially divaricated condition to enable the flow of blood through a lumen of the cardiac valve prosthesis in a first direction, and to a radially contracted condition, in which the set of prosthetic valve leaflets co-operate with one another and block the flow of blood through the cardiac valve prosthesis in a direction opposite the first direction.

8. The method of claim 1, wherein each set of anchoring formations extends bridge-wise between the corresponding arched strut and the annular part.

9. The method of claim 1, wherein the support posts are cantilevered to adjacent arched struts.

10. The method of claim 1, wherein the cardiac valve prosthesis is a replacement for an aortic valve.

11. The method of claim 1, wherein each set of anchoring formations comprises a pair of anchoring formations.

12. The method of claim 11, wherein deploying the cardiac valve prosthesis comprises positioning each pair of anchoring formations on opposite sides of a coronary ostia in the respective sinuses of Valsalva, thereby substantially avoiding interference with the coronary ostia.

13. The method of claim 1, further comprising sealing the cardiac valve prosthesis at the implantation site via a cuff covering the annular part and arranged outside of a lumen of the armature.

14. The method of claim 13, wherein the cuff is separate from the set of prosthetic valve leaflets.

15. The method of claim 1, wherein the annular part includes one or more coupling elements configured to be engaged by valve loading or crimping facilities or instruments.

16. The method of claim 1, wherein the sets of anchoring formations alternate with the support posts around a longitudinal axis of the cardiac valve prosthesis.

17. The method of claim 1, wherein each anchoring formation comprises a serpentine, a weaving, or an apertured pattern.

18. The method of claim 1, wherein each arched strut includes a distal portion at a distal end thereof which is substantially C-shaped and is configured to mate with a valve holder or a carrier portion of a delivery instrument.

19. The method of claim 1, wherein the plurality of arched struts includes inter-strut portions arranged at proximal ends, and the annular part has a mesh structure including cells and nodes, and
    wherein the inter strut portions have a Y-shape or a U-shape extending through the cells or nodes of the mesh structure of the annular part.

* * * * *